United States Patent [19]
de Radzitzky d'Ostrowick

[11] 3,931,091
[45] Jan. 6, 1976

[54] POLYVINYL CHLORIDE COMPOSITIONS PLASTICIZED WITH M-ETHYLPHENYL PHOSPHATE

[75] Inventor: Pierre M. J. G. de Radzitzky d'Ostrowick, Brussels, Belgium

[73] Assignee: Labofina S.A., Brussels, Belgium

[22] Filed: May 14, 1973

[21] Appl. No.: 360,368

[30] Foreign Application Priority Data
Oct. 27, 1972  Germany............................ 2252686

[52] U.S. Cl............................ 260/30.6 R; 260/966
[51] Int. Cl.²......................................... C08K 5/52
[58] Field of Search....................... 260/966, 30.6 R

[56] References Cited
UNITED STATES PATENTS

| | | | |
|---|---|---|---|
| 2,168,587 | 8/1939 | Shuman | 260/966 |
| 3,022,331 | 2/1962 | Bondy | 260/30.6 R |
| 3,125,529 | 3/1964 | Simmons | 260/966 |
| 3,549,730 | 12/1970 | Abadir | 260/966 |
| 3,576,923 | 4/1971 | Randell | 260/30.6 R |

*Primary Examiner*—Paul R. Michl

[57] ABSTRACT

A plasticized polyvinyl chloride composition and method for its preparation, the plasticized polyvinyl chloride composition comprising polyvinyl chloride and an organic phosphate selected from the group consisting of the phosphates of the formula $(C_6H_5)_x(m-C_2H_5C_6H_4)_y PO_4$, wherein $x$ is 0, 1 or 2 and $y$ is 1, 2 or 3, $x + y$ being 3, and mixtures of said phosphates, the amount of said organic phosphates being within the range of 20 to 100 parts by weight per 100 parts by weight of polyvinyl chloride.

6 Claims, No Drawings

POLYVINYL CHLORIDE COMPOSITIONS PLASTICIZED WITH M-ETHYLPHENYL PHOSPHATE

BACKGROUND OF THE INVENTION

This invention relates to plasticized polyvinyl chloride compositions and more particularly to polyvinyl chloride compositions containing an external plasticizer.

It is known that large amounts of plasticizers may be incorporated into polyvinyl chloride. This permits the processing of the resin to be made easier and also permits substantial improvement of the physical properties of the resin. The properties of polyvinyl chloride which may be improved by incorporating plasticizers depend upon the type of plasticizer. For example, when flexible vinyl plastics with flame-retardant properties are required, namely for floor coverings, electrical insulation and packaging, phosphate plasticizers and more particularly tricresyl phosphates are the most widely used.

Tricresylphosphate was one of the first plasticizers to be used with polyvinyl chloride. However, the poor low temperature properties of this phosphate, on one hand, and recurrent shortages of cresols, on the other hand, has led to efforts to substitute other plasticizers of the phsophate type for tricresyl phosphate. However, it appears that the improvement of one property of the vinyl resin generally takes place with accompanying detrimental changes of other properties when the heretofore known substitutes were tried. For instance, tri(ethylhexyl) phosphate imparts to polyvinyl chloride a better low temperature flexibility than tricresyl phosphate, but the plasticizer extraction by water or kerosene is drastically increased.

The object of the present invention is to provide plasticized polyvinyl chloride compositions wherein a new plasticizer of the phosphate type is employed.

Another object of the present invention is to provide a new and improved plasticized polyvinyl chloride wherein there is an improvement of the low temperature flexibility without detrimental effect or with little consequence on other valuable properties of the resin.

Still another object of the present invention is to provide a new and improved phosphate ester type plasticizer which may be substituted for tricresylphosphate as a plasticizer for polyvinyl chloride.

SUMMARY OF THE INVENTION

The present invention, which fulfills these and other objects, is a plasticized polyvinyl chloride composition containing polyvinyl chloride and an organic phosphate selected from the group comprising the phosphates of formula $(C_6H_5)_x(m\text{-}C_2H_5C_6H_4)_y PO_4$ where $x$ is 0, 1 or 2 and $y$ is 1, 2 or 3, the sum of $x$ and $y$ being 3, and mixtures of said phosphates, the amount of said organic phosphates present being between 20 and 100 parts by weight of the polyvinyl chloride present.

In another embodiment, the present invention is a method for plasticizing polyvinyl chloride resins, said method comprising incorporating within said polyvinyl chloride about 20 to 100 part by weight of an organic phosphate having the formula $(C_6H_5)_x(m\text{-}C_2H_5C_6H_4)_y PO_4$ wherein $x$ is 0, 1 or 2 and $y$ is 1, 2 or 3.

DESCRIPTION OF PREFERRED EMBODIMENTS

The phosphates of the present invention which contain at least one m-ethylphenyl group, are easily prepared by known methods. The starting m-ethylphenol should contain less than about 1% of its ortho-isomer and, preferably, should be practically free from this ortho-isomer. Indeed tri-(ortho-alkylaryl) phosphates are neurotoxic and mixed esters containing only one or two ortho-alkylphenyl groups are even more toxic. Tri-(para-ethylphenyl) phosphate is also toxic but mixed esters containing one or two meta-ethylphenyl groups and respectively two or one para-ethylphenyl groups are of quite reduced toxicity. It is therefore safe to use as a starting material, a meta-ethylphenol containing up to 10% but preferably, no more than 5% of para-isomer. For a sake of brevity, unless otherwise specifically indicated, the term meta-ethylphenol as hereinafter used includes not only substantially pure meta-ethylphenol, but also meta-ethylphenol containing less than 1% of ortho-isomer and also less than 10% of para-isomer.

The plasticizers of the present invention may contain 1 to 3 m-ethylphenyl groups and respectively 0 to 2 phenyl groups, impart noticeable properties to polyvinyl chloride and to copolymers containing primarily polyvinyl chloride. They are used in the usual range of concentration, more particularly in amounts which are higher than 20 parts per hundred parts by weight of polyvinyl chloride and which do not generally exceed 100 parts per hundred parts of PVC. The specific amount of plasticizer employed usually depends upon the required flexibility of the composition. The plasticizers according to the present invention may be selected from the group consisting of diphenyl-mono(m-ethylphenyl) phosphate, phenyl-di-(m-ethylphenyl) phosphate, tri(m-ethylphenyl) phosphate, and mixtures thereof. Although all of these plasticizers impart to polyvinyl chloride noticeably improved properties, tri(m-ethylphenyl) phosphate (hereinafter referred to as t-m EPP) preferably is used. In fact, compositions containing t-m EPP are characterized by good flexibility at low temperature and also by the stability of flexural properties as temperature is increased.

Comparative experiments have shown that polyvinyl chloride compositions containing t-m EPP are more flexible at low temperature than similar compositions containing other known organic phosphates. Table I gives the results of tests carried out on compositions containing 100 parts (by weight) of polyvinyl chloride, 50 parts of substantially pure t-m EPP and 5 parts of a conventional stabilizer (4 parts of tribasic lead sulphate and 1 part of lead stearate). Flexibility characteristics of these compositions at low temperatures have been measured according to ASTM procedure D-1043-69, with a Clash and Berg torsional tester. The value recorded is the temperature at which the sample had a modulus of elasticity of 3160 kg/cm$^2$ (or 45,000 pounds per square inch) and this value is designated as Tf.

Table I

| Plasticizer | Tf |
| --- | --- |
| Tricresyl phosphate | 9°C |
| Tri(dimethylphenyl) phosphate | 9°C |
| t-m EPP | −10°C |

These results show that the polyvinyl chloride composition containing t-m EPP retains its flexibility at low temperature more efficiently than compositions containing other known plasticizers of the phosphate type.

Another important feature of the compositions of the present invention is the stability of their flexural properties as temperature is increased. Previously used plasticizers, such as tricresyl phosphate, have a detrimental effect on the flow temperature of the composition. Polyvinyl chloride containing such known plasticizers in the usual range of concentration rapidly become too soft even at moderate temperatures. The variations in the rubbery state of compositions as hereinabove described have been measured with a torsional tester. The results are given in the following Table II.

Table II

| Plasticizer | Modulus at 25°C (A) | Modulus at 40°C (B) | Ratio A/B |
|---|---|---|---|
| Tricresylphosphate | 240 | 36 | 6.6 |
| t-m EPP | 85 | 50 | 1.7 |

The modulus and consequently the retention of mechanical strength of the compositions according to the present invention are less influenced by an increase of temperature, the ratio of the modulus being only 1.7, while this ratio is 4 times higher with the use of tricresylphosphate.

The better performances of the compositions according to the present invention are achieved without substantial loss or other valuable properties. More particularly, tests have been carried out on compositions containing respectively t-m EEP (substantially pure) and tricresylphosphate or other known phosphate plasticizers, with regard to efficiency of the plasticizer and resistance to extraction by environmental agents. The efficiency of the plasticizer has been determined by the 100% modulus, following the procedure outlined in ASTM-D-638. The 100% modulus is the load (in pounds per square inch) required to extend the polyvinyl chloride sample 100% in length; the lower the modulus, the greater the plasticizer efficiency. The % elongation (also according to ASTM-D-638) is the length to which a sample may be extended before rupture. Extraction tests have been carried out with hexane by dipping films of plasticized vinyl resin (0.5 mm thickness) into hexane at 23°C during 1 hr. and by measuring the weight loss. The vinyl resins were prepared from polyvinyl chloride, plasticizer and stabilizers as hereinabove defined. With respect to 100% modulus and % elongation (tests carried out at 25°C), t-m EPP is better than tricresylphosphate, as shown in Table III.

Table III

| | 100% modulus | % elongation |
|---|---|---|
| Tricresylphosphate (psi) | 1115 | 155 |
| t-m EPP | 900 | 170 |

Such results have not been obtained with other plasticizers of the phosphate type previously suggested as substituents for tricresylphosphate. In addition to the above results, t-m EPP gives better results than said other substituents with respect to extraction by such agents as hexane, as shown in Table IV.

Table IV

| | Hexane extraction % loss |
|---|---|
| t-m EPP | 3.1 |
| Tri(2-ethylhexyl) phosphate | 55.5 |
| 2-ethylhexyldiphenylphosphate | 5.50 |

These results show that t-m EPP is a particularly suitable plasticizer for vinyl resins. A similar test with t-m EPP prepared from meta-ethylphenol containing 5% of its paraisomer has given practically the same results, the % loss being 3.2.

Other phosphates containing m-ethylphenyl groups are also efficient plasticizers. For example, compositions have been prepared by mixing 100 parts (by weight) of polyvinyl chloride, 5 parts of the above specified stabilizers and:

50 parts of diphenyl-(m-ehtylphenyl) phosphate
50 parts of phenyl-di(m-ethylphenyl) phosphate
25 parts of each of these phosphates.
For each of these compositions, the % elongation was about 170%.

In the usual range of concentration, plasticizers of the phosphate type containing m-ethylphenyl groups impart to the plasticized compositions a number of improved important properties and are better than other flame-retardant plasticizers of the phosphate type.

Some improvements depend upon the amount of added plasticizer is shown in the following Table V, which gives results obtained from compositions containing 100 parts by weight of polyvinyl chloride, 5 parts of the above specified stabilizers and varying amounts of substantially pure t-m EPP (in parts per 100 parts of polyvinyl chloride)

Table V

| Amount of plasticizer | 30 | 50 | 70 |
|---|---|---|---|
| Elongation 100% | 130 | 170 | 260 |
| Tensile yield, psi | 3340 | 1950 | 1290 |
| Modulus at 100% elongation, psi | 1210 | 900 | 505 |

What is claimed is:

1. Plasticized polyvinyl chloride compositions comprising polyvinyl chloride and an a plasticizer consisting essentially of organic phosphate selected from the group consisting of the phosphates of the formula $(C_6H_5)_x(m-C_2H_5C_6H_4)_y PO_4$, wherein $x$ is 0, 1 or 2 and $y$ is 1, 2 or 3, $x + y$ being 3, and mixtures of said phosphates, the amount of said organic phosphates being within the range of 20 to 100 parts by weight per 100 parts by weight of polyvinyl chloride.

2. The plasticized polyvinyl chloride of claim 1 wherein said organic phosphate is tri(m-ethylphenyl) phosphate.

3. The plasticized polyvinyl chloride of claim 1 wherein said organic phosphate is one prepared from a metaethylphenol containing the para-isomer thereof in concentration of less than 10% by weight.

4. The plasticized polyvinyl chloride of claim 1 wherein said organic phosphate is one prepared from a metaethylphenol containing the ortho-isomer thereof in concentration of less than 1% by weight.

5. A process for plasticizing polyvinyl chloride comprising incorporating into a polyvinyl chloride polymer 20 to 100 parts by weight of an organic phosphate plasticizer per 100 parts by weight of polyvinyl chloride, said organic phosphate consisting essentially of one having the formula $(C_6H_5)_x(m\text{-}C_2H_5C_6H_4)_y$ $PO_4$, wherein $x$ is 0, 1 or 2 and $y$ is 1, 2 or 3, $x + y$ being 3.

6. The process of claim 5 wherein said organic phosphate is tri(m-ethylphenyl) phosphate.

* * * * *